United States Patent [19]
Yamada et al.

[11] Patent Number: 4,834,863
[45] Date of Patent: May 30, 1989

[54] OXYGEN SENSOR HAVING A HEATER

[75] Inventors: Toshio Yamada; Norio Oshima, both of Nagoya, Japan

[73] Assignee: NGK Insulators, Ltd., Japan

[21] Appl. No.: 21,658

[22] Filed: Mar. 4, 1987

[30] Foreign Application Priority Data

Mar. 5, 1986 [JP] Japan .............................. 61-30583[U]

[51] Int. Cl.$^4$ .......................................... G01N 27/58
[52] U.S. Cl. .................................. 204/429; 204/427; 204/428
[58] Field of Search ............... 204/424, 425, 427, 428, 204/429

[56] References Cited

U.S. PATENT DOCUMENTS

| | | |
|---|---|---|
| 4,512,871 | 4/1985 | Kato et al. ........................... 204/429 |
| 4,528,086 | 7/1985 | Kato et al. ........................... 204/429 |
| 4,657,660 | 4/1987 | Sato et al. ........................... 204/429 |

Primary Examiner—John F. Niebling
Assistant Examiner—Ben C. Hsing
Attorney, Agent, or Firm—Arnold, White & Durkee

[57] ABSTRACT

An excellent oxygen sensor having a heater with improved durability of the connecting portions of the lead terminals of the heater, is provided.

4 Claims, 2 Drawing Sheets

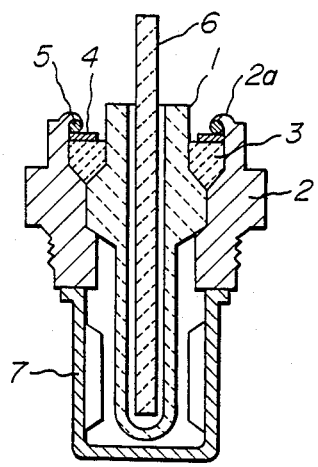
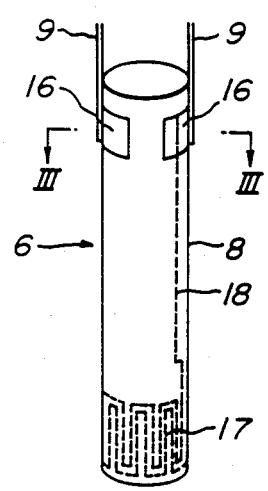

OXYGEN SENSOR HAVING A HEATER

BACKGROUND OF THE INVENTION

1. Field of the Invention

This invention relates to an oxygen sensor for detecting an oxygen content in a gas to be measured, such as an exhaust gas from an internal combustion engine, particularly to an oxygen sensor having a heater including a bottomed cylinder of a solid electrolyte having porous platinum electrodes on the inner and the outer surfaces thereof, the bottom or closed end of the cylinder being to be exposed in a gas to be measured, a housing accommodating the cylinder for gas tightly separating the inside of the cylinder from the gas to be measured, a protective metal cover or protector enclosing the outer circumferential surface of the closed end of the cylinder of the solid electrolyte and having at least one gas passage hole for the gas to be measured, and a rod-shaped heater inserted in the interior of the cylinder of the solid electrolyte.

2. Description of the Prior Art

Heretofore, oxygen sensors have been known which detect oxygen concentrations of gases exhausted from internal combustion engines, such as automobile engines etc. by using oxygen ion-conductive solid electrolytes, such as zirconia etc., based on the principle of oxygen concentration cell, to control air/fuel (A/F) ratio of the internal combustion engines. Usually, this type of oxygen sensor is provided with a bottomed cylinder of a solid electrolyte made of zirconia, and porous platinum electrodes formed on the inner and the outer surfaces of the zirconia cylinder, the inner electrode being communicated with the exterior atmosphere to form a standard electrode of a standard oxygen concentration, and the outer electrode being exposed to a gas to be measured such as an exhaust gas from an automobile engine to form a measuring electrode, and measures an electromotive force resulted from a difference of oxygen concentrations between the standard electrode and the measuring electrode to determine an oxygen concentration in the gas to be measured.

However, the oxygen sensor does not generate a stable electromotive force, unless the solid electrolyte is heated to a sufficient extent. Therefore, it has a drawback in that the A/F ratio can not be controlled exactly at an idling state or immediate after the start of the internal combustion engine where the solid electrolyte of the oxygen sensor is still cold.

In order to solve the above drawback, various methods of forcibly heating the solid electrolyte have been proposed. For example, U.S. Pat. No. 4,155,827 discloses insertion of a heater composed of a heater wire wound on a rod-shaped insulator surface in the interior of the solid electrolyte, and U.S. Pat. No. 4,212,720 disclosed insertion of a so-called "sheath heater" composed of a metal sleeve and a resistive coil and a good thermally conductive and electrically non-conductive powder filled in the metal sleeve in the interior of the solid electrolyte.

However, this type of conventional oxygen concentration detectors or oxygen sensors having a heater have drawbacks in that when the temperature of the exhaust gas from an internal combustion engine becomes high, the solid electrolyte is suffered from excessive heating so that the porous platinum electrodes recrystallize to retard the rate of response to the exhaust gas, that a spinel coating layer protecting the porous platinum electrodes is peeled off or yields a crack, and that the heater per se becomes to an extraordinary high temperature due to heat generation thereof together with the heating thereof by the exhaust gas to break down the resistive wire therein.

If the amount of heat generated by the heater is suppressed to a small value for mitigating the above problems as far as possible, then another problems are incurred in that the solid electrolyte is insufficiently heated when the temperature of the exhaust gas is low, and that it takes a long time before the oxygen concentration detector generates an exact electromotive force, even when the heating is effected from the start of the engine.

Moreover, the battery voltage decreases at the time of starting the engine or at the time of cold climate, so that the problems of insufficient heating are even more accelerated. While, at the time of high revolution rate of the engine and elevated state of the battery voltage, the temperature of the exhaust gas becomes also high and the amount of heat generated by the heater is also increased, so that the problems of excessive heating are also even more accelerated.

Furthermore, a phenomenon of migration of silver occurs which results from a prolonged passage of an electric current through the brazing element containing the silver, so that a drawback also arises in that the brazed portions of the lead terminals of the heater are short-circuited therebetween.

In order to obviate these drawbacks, U.S. Pat. No. 4,512,871 (Japanese Utility Model Application Laid-Open No. 60-106,160) proposed an oxygen detector having a heater which comprises, a bottomed cylinder of a solid electrolyte 1 having porous platinum electrodes on the outer and the inner surfaces thereof as shown in FIG. 1, a rod-shaped heater 6 inserted in the interior of the solid electrolyte 1. The rod-shaped heater 6 is composed of a ceramic heater body 8, and a heating element 17 embedded in the ceramic heater body 8, lead portions 18 of the heating element 17 communicating the heating element 17 with the connecting portion 16, lead terminals 9, and connecting portions 16 for connecting the lead terminals 9 to the heater body 8, as shown in FIG. 2. Each connecting portion 16 is provided with a heater lead layers 15 communicated with the heater body 8, a metal plating layer 10 applied on the heater lead layer 15, the lead terminal 9 being fixed on the metal plating layer by brazing by a brazing element 11 containing silver, a metal coating layer 12 consisting of an electroless plating layer of metal other than silver, such as nickel, applied on the brazing element 11, as shown in FIG. 4.

As shown in FIG. 4, the lead terminal 9 consisting of a nickel wire is fixed to the metal layer 10 consisting of a plating layer of nickel by brazing by means of the brazing element 11, the metal layer 10 being applied on the ceramic heater body 8 made of alumina or the like via a heater lead layer 15 made of tungsten. Therefore, when using the oxygen sensor after assembled, the metal plating layer 10 which forms the brazing part of the lead terminal of the heater is influenced by temperature change of the exhaust gas of the internal combustion engine or temperature cycle caused by ON-OFF of the heater at the time of starting the engine or stopping the engine. Thus, a heat cycle is repeatedly imposed on the metal plating layer 10. As a result, there are hitherto problems that a crack occurs on the ceramic body 8 of the heater, and that the lead terminal 9 is disengaged from the heater body 8. Besides, the heater lead layer 15 made of tungsten can not be directly brazed by a brazing element, so that the metal plating layer 10 such as nickel plating has to be applied thereon for accomplishing the brazing.

SUMMARY OF THE INVENTION

An object of this invention is to obviate the aforementioned problems.

Another object of this invention is to improve the durability of the connecting portions of the lead terminals of the ceramic heater of the oxygen sensor.

For achieving the above objects, a metal piece having a linear expansion coefficient different from that of the lead terminals is fixedly brazed on the metal plating layer such as nickel via a thin brazing element layer, in this invention.

This invention is an oxygen sensor comprising:
a cylindrical solid electrolyte body which includes an open first end, a closed second end and inner and outer surface having porous platinum electrode layer;
a metal housing which receives said cylindrical solid electrolyte body therein;
a protective metal cover which encloses said closed second end of the cylindrical solid electrolyte and has at least a gas passage hole for the gas to be measured; and
a ceramic heater which is inserted in the interior of said cylindrical solid electrolyte,
wherein said ceramic heater has a heating element of a positive resistant-temperature coefficient, a ceramic body embedding said heating element therein, a connecting portion arranged on the outer surface of said ceramic body and communicating with said heating element, and a lead terminal for a power source fixed on a metal piece having a linear thermal expansion coefficient different from that of said lead terminal wherein said metal piece are brazed on said heater lead portion.

The linear thermal expansion coefficient of the metal piece should be smaller than that of the brazing element, and the linear expansion coefficient of the metal piece is preferably be smaller than that of the lead terminals. Preferably, the linear thermal expansion coefficient of the metal piece is equal or nearly to that of the ceramic heater body.

BRIEF DESCRIPTION OF THE DRAWINGS

For a better understanding of this invention, this invention will be explained in more detail with reference to the accompanying drawings, in which:

FIG. 1 is a schematic crosssectional view of an embodiment of the oxygen sensor having a heater of this invention;

FIG. 2 is a schematic perspective view of an embodiment of a rod-shaped heater used in the oxygen sensor of this invention;

Figure 3A:
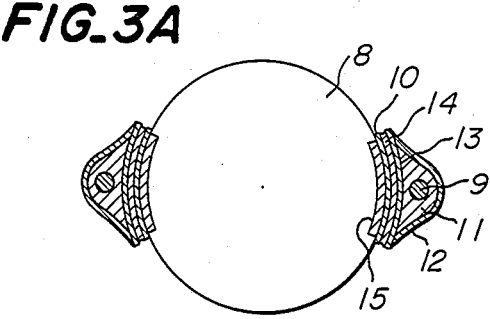
FIG. 3A is a schematic crosssectional view of the rod-shaped heater taken along the line III—III of FIG. 2.

Throughout different views of the drawings, reference numeral 1 is a bottomed cylinder of a solid electrolyte, 2 is a housing, 2a is a caulking portion of the housing 2, 3 is talc filling, 4 is a washer, 5 is a ring, 6 is a rod-shaped ceramic heater, 7 is a protective cover, 8 is a ceramic heater body, 9 is a lead terminal, 10 is a metal plating layer, 11 is a brazing element, 12 is a nickel plating layer, 13 is a metal piece, 14 is a brazing element, 15 is a heater lead layer, and 16 is a connecting portion of the lead terminal 9 is a heating element, and 18 is lead portions of the heating element 17.

DESCRIPTION OF THE PREFERRED EMBODIMENT

Hereinafter, this invention will be explained in more detail by referring to a preferred embodiment illustrated in the drawings.

Referring to FIG. 1, the bottomed cylindrical body of a solid electrolyte 1 having respective porous platinum electrode on the inner and the outer surfaces thereof is mounted on an exhaust gas pipe (not shown) and exposed to an exhaust gas passing therethrough. The bottomed cylindrical body 1 is received in the housing 2, and caulked by the caulking portion 2a of the housing 2 via the talc filling 3, the metal washer 4 and the metal ring 5 so as to keep the interior of the housing 2 gastight. In the cylindrical body 1 of the solid electrolyte the rod shaped heater 6 is accommodated. The metal housing 2 is provided with at its lower end the protective metal cover 7 surrounding the outer circumferential surface of the closed end of the cylindrical body 1 to protect the cylindrical body 1 from direct impingement of the exhaust gas thereto.

The rod-shaped heater 6 used in the oxygen sensor of FIG. 1 is composed of the ceramic heater body 8 in which a heating element 17 is embedded, and the lead terminals 9 fixed to the ceramic heater body 8 by brazing, as shown in FIG. 2. Further detailed structures of the brazed fixed portion of the heater 6 are shown in FIGS. 3A and 3B taken along the line III—III of FIG. 2.

Figure 3B:
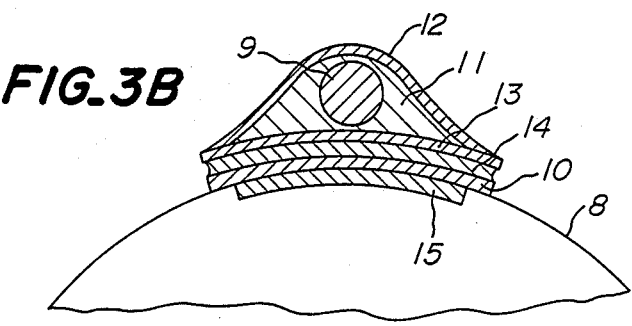
FIG. 3B is a schematic enlarged view thereof.

Referring now to FIGS. 3A and 3B, a metal plating layer 10 such as nickel or the like is applied on the circumferential side surface of the ceramic heater body 8 made of alumina etc. via the heater lead layer 15 consisting of hardly fusible electrically conductive metal such as tungsten or molybdenum etc. The metal plating layer 10 is coated with the metal piece 13 having a linear thermal expansion coefficient different from that of the lead terminal 9 by brazing via the brazing element 14. To the metal piece 13 is fixed the lead terminal 9 consisting of an electrically conductive metal such as copper, nickel or the like by welding or brazing by means of the brazing element 11. The nickel plating layer 12 may be applied on the brazing element 11, if desired.

The lead terminal 9 can be brazed or welded at any place of the metal piece 13, e.g., at the edge surface of the metal piece 13, unless there is any other objection.

The reason why the metal plating such as nickel plating is applied on the heater lead layer 15 and on the brazing member 11 brazing the lead terminal 9 is that there is the necessity of preventing the migration of the silver in the brazing element 11 when the oxygen sensor is used in a high humid and high temperature circumstance and a voltage is applied across the rodshaped ceramic heater 6.

The brazing element layer 14 applied on the metal plating layer 10 is preferably thin of below 50 $\mu$m. If it is thick, it can not act to mitigate or buffer a thermal expansion difference between the cold state and the hot state of the brazing element layer 14.

The linear thermal expansion coefficient of the metal piece 13 should be different from that of the lead terminal 9, and the former is preferably be smaller than the latter. The linear thermal expansion coefficient of the metal piece 13 is preferably be smaller than that of the brazing element 14. While, the linear thermal expansion coefficient of the metal piece 13 should preferably be equal or nearly to that of the ceramic heater body.

The interrelations between these materials may be exemplified in Table 1.

TABLE 1

| Parts | Material | Linear Thermal Expansion Coeff. ($10^{-7}$/deg) | Specific Resistance ($\mu\Omega \cdot m$) |
|---|---|---|---|
| Metal Piece | Kovar (Ni—Co—Fe alloy) | 40–80 | 0.49 |
| | Fe—42% Ni alloy | 40–50 | 0.70 |
| Brazing Element | Silver braze | 150–200 | 0.016 |
| Lead Terminal | Nickel wire (30–400° C.) | 130 | 0.069 |
| | Copper wire (30–400° C.) | 177 | 0.017 |
| Ceramic Heater Body | Alumina | 80 | — |
| | Spinel | 80 | — |
| Heater Lead Layer | Tungsten | — | 0.056 |

In case when the lead terminal is long or thin, the lead terminal is preferably be made of nickel (Ni), copper (Cu) or other low resistance material.

The structure of the low resistance lead terminal welded or brazed to the metal piece (for example, Kovar (trade name) have larger resistances than the lead terminal by one order) exhibits advantageous effects of preventing an occurrence of disorder of the terminal portion and a damage of the lead terminals caused by high voltage.

As apparent from the above Table 1, when the ceramic has a linear thermal expansion coefficient value of $80 \times 10^{-7}$/° C. and the metal piece is Kovar etc., the linear thermal expansion coefficient value of the metal piece can be selected also to $80 \times 10^{-7}$/° C. And, when the lead terminal is a nickel wire and its linear thermal expansion coefficient value is $130 \times 10^{-7}$/° C. and the linear expansion coefficient value of the brazing element is $150 \times 10^{-7}$/° C., the coefficient value of the metal piece is smaller than those of the lead terminal and the brazing element and equal or approximate to that of the ceramic heater body, so that thermal expansion can be mitigated as compared with the case of omitting the metal piece, resulting in the prevention of the crack formation on the ceramic body.

If a silver braze is used to the connecting portion 16 of the lead terminal 9, a nickel plating layer 12 or an inorganic coating can be applied on the brazed portion for preventing the migration of the silver particles.

This invention will now be described in further detail by referring to an example.

EXAMPLE 1

Durability comparison tests are effected selecting the following components.
Ceramic heater body 8: alumina
Heater lead layer 15: tungsten
Metal plating layer 10: nickel
Brazing element 14: Silver-copper eutectic alloy
Metal piece 13: Kovar
Brazing element 11: Silver-copper eutectic alloy
Lead terminal 9: nickel wire Selecting the above components or composition, ten samples of the oxygen sensor of this invention having the heater as shown in FIGS. 3A and 3B are prepared by providing the heater lead layer 15 made of tungsten on the ceramic heater body 8 made of alumina, providing the nickel plating layer 10 on the heater lead portion 15, brazing the metal piece 13 on the nickel plating layer 10 via the brazing element 14, and brazing or welding the lead terminal 9 on the metal piece 13 by means of the brazing element 11.

Figure 4:
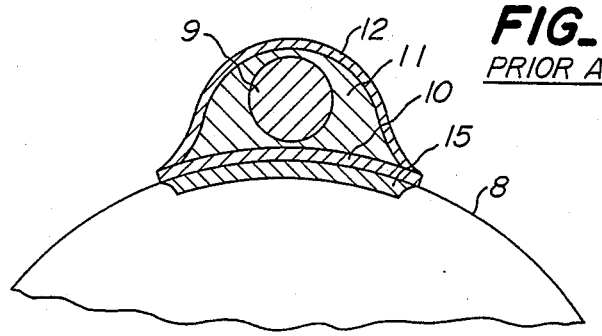
FIG. 4 is a schematic crosssectional view of a heater of a conventional oxygen sensor, corresponding to the heater according to this invention of FIGS. 3A and 3B.

For comparison use, ten more samples of conventional oxygen sensor having heater as shown in FIG. 4 are prepared using the same components, except that the metal piece 13 and the brazing element layer 14 are omitted from the oxygen sensor of FIGS. 3A and 3B of this invention.

Electric current is applied to each ceramic heater of these oxygen sensors, and the power source of the ceramic heater is switched on or off at an interval of 15 minutes, with an atmosphere temperature of 50° C. for the switched-off state and 250° C. for the switched on state, and the switching on and off operation is repeated for 400 times. The results are shown in the following Table 2.

TABLE 2

| This Invention | Prior Structure | | |
|---|---|---|---|
| 10/10 | 1/10 | 7/10 | 2/10 |
| No problem | Peeled off | Crack occurred | No problem |

As seen from the above Table 2, one oxygen sensor of the prior structure had a failure or defect and seven showed occurrence of crack. All the ten oxygen sensors of this invention showed no peeling-off or crack-occurrence, so that the oxygen sensor of this invention passed the durability test at the percentage of 100%. Thus, this invention has a splendid effect of remarkably improving the durability of the oxygen sensor.

This invention improved the connecting portions of the lead terminals of the ceramic heater of the oxygen sensor having the heater to enhance its durability extensively, so that this invention is eminently useful in industry.

Although the present invention has been explained with reference to specific examples and numeral values, it is of course apparent to those skilled in the art that various changes and modifications are possible without departing from the broad spirit and aspect of the present invention as defined in the appended claims.

What is claimed is:
1. An oxygen sensor comprising:
a cylindrical solid electrolyte body which includes an open first end, a closed second end and inner and outer surfaces having porous platinum electrode layers;
a metal housing wherein said cylindrical solid electrolyte body is disposed;
a protective metal cover which encloses said closed second end of the cylindrical solid electrolyte body, said cover including at least a gas passage hole for a gas to be measured; and
a ceramic heater which is inserted in the interior of said cylindrical solid electrolyte body,
wherein said ceramic heater has a positive resistant-temperature coefficient heating element, a ceramic heater body embedding said heating element therein, a connecting portion arranged on the ceramic heater body, said connecting portion communicating with said heating element through lead portions of said heating element and a heater lead layer arranged on an outer surface of said ceramic heater body and communicating with said connecting portion, said connecting portion consisting essentially of a metal plating layer arranged on an outer surface of said heater lead layer, a metal piece brazed, by way of a brazing element, on the metal plating layer, and lead terminals, for connection to a power source, brazed on said metal piece, said metal piece having a linear thermal expansion coefficient which is different from that of said lead terminals and approximately equal to that of said ceramic heater body.

2. An oxygen sensor having a heater as defined in claim 1, wherein the metal piece has a smaller linear thermal expansion coefficient than that of the brazing element.

3. An oxygen sensor having a heater as defined in claim 1, wherein the metal piece has smaller linear thermal expansion coefficient than that of the lead terminal.

4. An oxygen sensor having a heater as defined in claim 1, wherein the metal piece is a Ni—Co—Fe alloy, the brazing element is silver, and the ceramic heater body consists essentially of alumina.

* * * * *